(12) United States Patent
Bublitz et al.

(10) Patent No.: US 9,084,564 B2
(45) Date of Patent: Jul. 21, 2015

(54) SYSTEM FOR DETERMINING THE TOPOGRAPHY OF THE CORNEA OF AN EYE

(75) Inventors: Daniel Bublitz, Rausdorf (DE); Günter Rudolph, Jena (DE); Martin Hacker, Jena (DE); Tobias Bühren, Magdala (DE); Roland Bergner, Jena (DE); Burkhard Wagner, Jena (DE); Rico Fuchs, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 14/119,367

(22) PCT Filed: May 22, 2012

(86) PCT No.: PCT/EP2012/059458
§ 371 (c)(1),
(2), (4) Date: Nov. 21, 2013

(87) PCT Pub. No.: WO2012/160049
PCT Pub. Date: Nov. 29, 2012

(65) Prior Publication Data
US 2014/0078468 A1  Mar. 20, 2014

(30) Foreign Application Priority Data
May 24, 2011  (DE) .......................... 10 2011 102 355

(51) Int. Cl.
*A61B 3/107* (2006.01)
*G01B 11/25* (2006.01)

(52) U.S. Cl.
CPC ............ *A61B 3/107* (2013.01); *G01B 11/2513* (2013.01)

(58) Field of Classification Search
CPC .................................. A61B 3/107; A61B 3/10

USPC .................. 351/205, 212, 246; 359/708, 709
See application file for complete search history.

(56) References Cited

U.S. PATENT DOCUMENTS 4,660,946 A   4/1987  Nakamura et al.
4,685,140 A   8/1987  Mount, II
(Continued)

FOREIGN PATENT DOCUMENTS

DE   1 572 779        5/1970
DE   19636472 A1     3/1998
(Continued)

OTHER PUBLICATIONS

Golub I, "Fresnal Axicon", Optics Letters, Jun. 15, 2006, The Optical Society, vol. 31, No. 12, pp. 18-90-1892, XP001243271.
(Continued)

*Primary Examiner* — Scott J Sugarman
*Assistant Examiner* — William R Alexander
(74) *Attorney, Agent, or Firm* — Patterson Thuente Pedersen, P.A.

(57) ABSTRACT

A system for determining the surface shape of the cornea of an eye by analyzing the reflection of a spatially distributed ring pattern. The system includes an element for generating a ring pattern, an illuminating unit, an image capturing unit, and a control and analyzing unit. The element for generating rings is a fresneled axicon with annular structures of different radii. Furthermore, an optical element for illuminating the entire surface of the fresneled axicon with plane waves and an optical element for separating the illuminating and detecting beam path are arranged between the illuminating unit and the fresneled axicon. Furthermore, the image capturing unit consisting of an imaging system and an image sensor is designed for a telecentric distance-independent image detection.

31 Claims, 6 Drawing Sheets

(56) References Cited

U.S. PATENT DOCUMENTS

| | | |
|---|---|---|
| 5,110,200 A | 5/1992 | Snook |
| 5,194,882 A | 3/1993 | Penny |
| 5,684,562 A | 11/1997 | Fujieda |
| 5,864,383 A | 1/1999 | Turner |
| 6,048,065 A | 4/2000 | Davis et al. |
| 6,070,981 A | 6/2000 | Mihashi et al. |
| 6,116,738 A | 9/2000 | Rorabaugh |
| 6,575,573 B2 | 6/2003 | Lai et al. |
| 6,692,126 B1 | 2/2004 | Zie et al. |
| 2003/0071968 A1 | 4/2003 | Lai et al. |
| 2008/0123053 A1* | 5/2008 | Mihashi et al. ............... 351/221 |
| 2010/0302396 A1* | 12/2010 | Golub et al. ............... 348/222.1 |
| 2011/0222020 A1* | 9/2011 | Izatt et al. ..................... 351/205 |

FOREIGN PATENT DOCUMENTS

| | | |
|---|---|---|
| EP | 1 138 254 A1 | 10/2001 |
| EP | 0 843 529 B1 | 6/2002 |

OTHER PUBLICATIONS

International Preliminary Report on Patentability for International Application No. PCT/EP2012/059458 dated Dec. 5, 2013, 9 pages.

\* cited by examiner

SYSTEM FOR DETERMINING THE TOPOGRAPHY OF THE CORNEA OF AN EYE

RELATED APPLICATIONS

The present application is a National Phase entry of PCT Application No. PCT/EP2012/059458, filed May 22, 2012, which claims priority from DE Application No. 10 2011 102 355.4, filed May 24, 2011, which applications are hereby incorporated by reference herein in their entirety.

FIELD OF THE INVENTION

The present invention relates to a system of determining the surface shape of the cornea of an eye by analyzing the reflection of a spatially distributed pattern, especially a ring pattern similar to a Placido disk.

The Placido disk is an illuminated disk that generates a known pattern in the form of circles at regular intervals and is reproduced on the eye. Diagnosis is then made by viewing the reflection of the circles on the surface of the cornea, on which the circles should be reproduced with the same regularity.

Now a symmetrical reflection of the concentric Placido rings should be visible on the corneal surface. If there are rings with an asymmetrical shape, however, this is an indication of that the corneal surface deviates from a reference surface. Irregularities of the corneal surface may be found e.g. with an astigmatism, but also with mechanical or chemical injuries to the cornea.

The term keratometry shall be construed as the measurement of shape and form of the cornea of the eye. An ophthalmometer (also known as a keratometer) measures the radii of curvature of the cornea centrally and in the periphery. The measured radii are for instance the basis for fitting contact lenses. One particular form of keratometry is topography. Topography uses special methods to measure and mathematically analyze the central and peripheral radii of curvature of the cornea.

Measuring the surface of the cornea of the human eye proves to be difficult because the cornea is transparent and no significant amount of visible light is backscattered.

The cornea is the front-most section of the eye and has a specific geometry that curves forward. Topography is used to measure this geometric shape of the front surface of the cornea in its entirety. The front surface shape may vary, two of the most important and also generally well known shapes being the spherical (round) cornea and the astigmatic (distorted) cornea.

Having refractive power of more than 40 diopters, the cornea is a critical factor for the refraction of light entering the eye. Corneal refractive power is primarily a function of the shape of the corneal surface and in particular its curvature. Determining the shape of the corneal structure is extremely important in the following areas in particular:

Cataract surgery, in connection with reducing astigmatism
Contact lens fitting
Detecting keratoconus
Corneal determination of astigmatism
Refractive surgery
Creating suitable eyeglasses.

In surgical applications, determining the surface shape of the cornea of an eye is important both before and after the surgical intervention because the surface shape is suitable for detecting anomalous or abnormal corneal shapes.

Methods for measuring the corneal surface shape using so-called keratometers or keratographs have been known for some time in the prior art. The concentric rings of the Placido disk reproduced on the cornea are reflected by the pre-corneal tear film and are recorded and analyzed with a camera. The reflected ring pattern that is detected by the camera is distorted as a function of the curvature of the cornea. To determine the curvature from these reflection signals, the distortions of the rings must be compared to a known shape, which is generally selected as a sphere having a radius of 7.8 mm. U.S. Pat. No. 4,685,140 A describes such a solution, for instance.

The Placido disk used in topography for generating concentric rings does not necessarily have to be a planar disk. Although such planar Placido disks are sufficiently known in the prior art and are described for instance in U.S. Pat. No. 5,110,200 A and U.S. Pat. No. 5,194,882 A, funnel-shaped (U.S. Pat. No. 5,684,562 A, U.S. Pat. No. 6,116,738 A) and even spherically curved (U.S. Pat. No. 5,864,383 A) Placido disks are more widely used.

U.S. Pat. No. 4,660,946 A describes a solution for measuring the shape of the cornea, which solution is based on a disk-shaped Fresnel cylinder lens. For projecting the ring structure onto the eye, each ring of the Fresnel cylinder lens is illuminated individually, in rings, by means of the ring cylinder lens. Due to the disk-shaped structure, the number of realizable rings is limited, and in addition this type of illumination is very difficult to achieve as the number of rings increases. U.S. Pat. No. 6,575,573 B2 and U.S. Pat. No. 6,692,126 B1 describe solutions for ophthalmometers (also called keratometers) that are supplemented with a slit illumination device. While the reproduction of Placido ring systems is provided for measuring the surface curvature of the cornea of the eye, the slit illumination unit generates sectional images of the eye from which the thickness of the cornea of the eye may be determined. As a result of this combination it is possible to determine a corneal thickness profile.

This method has the advantage that for measuring the corneal surface shape only a single recording that includes a large number of data points at a high spatial resolution is required. Because only a single recording is required, eye movements have no effect on the accuracy of the measurement. One drawback of this type of solution is that the images captured by the camera include an image of the eye, in particular its iris and the parasitic image of the Placido rings projected onto the tear film in front of the cornea as an overlay.

However, for an exact determination of the surface topography of the eye, the analysis algorithm must detect the Placido rings perfectly. The problem that may occur is that the overlaid iris structure may interfere with detection of the Placido rings because in some circumstances the edge of the pupil can be confused with the rings.

Commercially available topography systems project real Placido rings at a short distance in front of the eye onto the cornea, from where they are reflected and detected with a camera. The corneal reconstruction is based on angular evaluation of angles of incidence and emergent angles of the projected Placido rings and Placido rings that are reflected by the cornea. The deviation in the ring position on the cornea relative to the ring position of a known reference test body is the basis for the corneal reconstruction. A second drawback of such solutions is that the accuracy of the measurement is highly dependent on the angular ratios and thus on the measurement distance.

Many different methods are used for determining or for controlling the correct measurement distance. For instance, the measurement may be initiated automatically when the correct working distance is attained. This may occur due to a correction to the incorrect distance before each measurement in that the distance or the position is determined using light barriers, contacts, or additional measuring systems and, where necessary, corrected.

U.S. Pat. No. 6,048,065 A and U.S. Pat. No. 6,070,981 A are cited as examples of this. The solutions described therein represent topographs that are based on a Placido disk. For controlling the correct measuring distance, both solutions have a point light source, the light of which is projected onto the cornea, reflected thereby, and reproduced on a CCD camera as a point image. The position of the point image within the capture area provides information about the distance between Placido disk and eye. For exact positioning, the Placido disk is displaced until the distance is optimized. Only then does the measurement begin.

In the solutions described in EP 0 843 529 B1 and EP 1 138 254 A1, the correct measuring distance is controlled or corrected using two additional cameras that are each arranged laterally, right and left, from the head. It is provided that both the two laterally arranged cameras and the main camera arranged on the optical axis for measuring the cornea are arranged fixed with respect to one another. The entire system is positioned with respect to the eye or cornea to be measured such that an optimum measuring position is attained, depending on the images captured by the laterally arranged cameras.

In addition, however, the measurements made at non-optimum distances may be appropriately corrected in that certain correction algorithms are used for cases in which for instance non-optimum measuring distances were found by an image analysis. The "incorrect" measurement results may be corrected using appropriate correction algorithms.

The most used corneal topography system in the world from Carl Zeiss Meditec is called ATLAS™ and has such correction algorithms. With its powerful and user-friendly software platform, the ATLAS™ system supplies precise, reliable, and reproducible results at each examination and practically for each user.

Using the patented, so-called Cone of Focus™ alignment system, ATLAS™ ensures that the cornea to be measured is aligned correctly with the measuring system. This happens based on triangulation with Cone of Focus™ in conjunction with the Placido disk, which is also patented.

Although this method provides precise, reliable, and reproducible results for the majority of eyes to be examined, i.e. eyes with "normal" curvatures of the cornea, problems may occur when there "abnormal" curvatures of the cornea. Such an "abnormally" curved cornea may be caused e.g. by a previous condition such as keratoconus.

In order to measure the exact angular ratios, the distance from the device to the location of the eye to be examined at which the radiation from a Placido ring is reflected must be known. Therefore actually not only must the distance between the eye and the measuring device on the optical axis be known, but in addition the entire shape of the cornea, which is first to be measured, however, must actually be known. As a solution to this problem, it is possible to employ interactive algorithms that minimize the effect of this problem on the measurement results. However, these algorithms combine the measurement inaccuracies for all rings due to error propagation and the results are thus inaccurate depending on data quality. In patients with healthy cornea shapes this problem may be overcome using very high measuring quality, but very major measurement deviations may occur with corneas that are abnormally deformed.

Exact, highly precise alignment in the range of less than 1 micrometer is the requirement for high precision measurements during each examination. The SmartCapture™ image analysis system analyzes up to 15 digital images per second during the alignment and automatically selects the image with the best quality.

The idea of precisely examining and measuring the cornea of the human eye is already quite old. The first classical keratometer was developed in 1856 by H. von Helmholz. The measuring method that could be performed using this keratometer is the same as the measuring method still used today. However, Helmholz's keratometer was very unwieldy.

It is all more astonishing that Littman did not create an entirely distance-independent keratometer until 1950. For distance-independent keratometers, adjustments in image sharpness cannot be influenced by the accommodation of the observer and ametropia, which eliminates the greatest deficiencies of distance-independent devices.

In the Littmann keratometer, virtual test symbols are projected that are infinitely reproduced on the cornea via a lens. Thus the distance dependency for the measurement is a function only of the depth of field of the camera acting as the optical observation system, but is not dependent on test symbol distance. Distance-independence for image detection is attained using a telecentric beam path. Measurement accuracy with respect to distance between eye and device is significantly reduced and the measurement results are therefore very reproducible. In addition, it was possible to reduce the number of measurement and reading errors and to accelerate the measuring processes.

However, the low number of measuring points in Littmann keratometers proved to be a drawback. While in Littmann keratometers only 2 to 8 measuring points are produced, there are several thousand measuring points for topography based on Placido disks.

Keratometers in which for instance 6 individual collimated light sources illuminate the cornea at specific angles represent a completely distance-independent technical solution. The essential advantage of such methods is the very precise, quantitative measurement of the curvature of the cornea. Thus, the IOLMaster® from Carl Zeiss Meditec AG, which is based on a short coherent method, represents an optical measuring device according to this principle.

It is a drawback of this method that the cornea is measured at only a few points and thus there may be measurement errors, in particular for corneas that have additional surface deformations in addition to curvature and astigmatism. For such exceptional cases, a great number of measurement points, similar to a Placido disk, would be advantageous. However, since a separate source with imaging optics is necessary for each measuring point, the technical complexity is that much greater.

DE 1 572 779 provides a method in which the illumination is provided using a filter whose plurality of narrow, annular, concentric apertures are reproduced in the eye to be measured using an optics unit. As in all of the methods described in the foregoing, detection occurs through the center of the ring system using a telecentrically corrected optics unit along the optical axis. Distance-independence for the illumination is attained in that the eye is illuminated with a plurality of "annularly plane" waves. Thus, the corresponding primary plane that is the resultant focal length of the optics unit that reproduces the rings in the eye is the same distance from the annular filter as from the cornea of the eye. A drawback of this method is the relatively high technical complexity for this imaging optics unit, since a plurality of lenses must be employed to attain the required high accuracy and to be able to compensate spherical errors that occur. Another drawback is the low light efficiency that results from the relatively narrow annular filter widths.

SUMMARY OF THE INVENTION

The underlying object of the present invention is to develop a system for determining the topography of the cornea of an eye, which system permits largely distance-independent measurements in a fairly large measuring area and given severe asphericity permits and generates for it a plurality of measurement points. A technical embodiment that has higher light efficiency and thus may be produced in a much simpler manner, and thus more cost effectively, shall be used for illumination.

The underlying object is attained with the system for determining the topography of the cornea of an eye, comprising an element for generating rings similar to Placido disks and an illuminating unit that are arranged in an illuminating beam path and comprising an image capturing unit arranged in a detecting beam path and a control and analysis unit, in that the Placido disk-like element is embodied as a fresneled axicon having annular structures of different radii, in that an optical element for illuminating the entire surface of the fresneled axicon with plane waves and an optical element for separating illuminating and detecting beam paths are arranged between the illuminating unit and the fresneled axicon, and in that the image capturing unit, comprising an imaging system and an image sensor, is embodied for telecentric, distance-independent image detection.

The suggested system is suitable for determining the topography of reflecting bodies. In particular, however, it is for determining the topography of the cornea of an eye.

BRIEF DESCRIPTION OF THE DRAWINGS

The invention shall be described in greater detail in the following using exemplary embodiments.

For each figure, the surface of the element that faces the cornea is called the front side. The front side is always depicted on the left, even if the cornea is not shown.

DETAILED DESCRIPTION

The inventive system for determining the topography of the cornea of an eye comprises an element for generating rings similar to Placido disks and an illuminating unit that are arranged in an illuminating beam path, and comprises an image capturing unit arranged in a detecting beam path and a control and analyzing unit. The element for generating rings similar to Placido disks is a fresneled axicon having annular structures of different radii. Moreover, an optical element for illuminating the entire surface of the fresneled axicon with plane waves and an optical element for separating the illuminating and detecting beam paths are arranged between the illuminating unit and the fresneled axicon. In addition, the image capturing unit, comprising an imaging system and an image sensor, is embodied for telecentric, distance-independent detection.

A first group of example embodiments relates to the fresneled axicon, which is the element for producing rings. The annular structures having different radii may be arranged in the form of facets on the front and/or back sides of the fresneled axicon.

Figure 1:
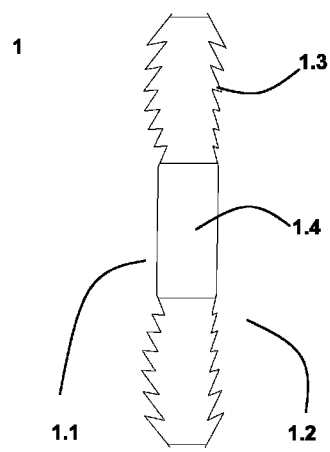
FIG. 1 is a schematic diagram of the inventive fresneled axicon with facets on the front and back sides.

FIG. 1 is a schematic diagram of an example embodiments of an inventive fresneled axicon having facets on the front and back sides.

Present on both the front side 1.1 and on the back side 1.2 of the fresneled axicon 1 are facets 1.3 that direct the light from the illumination source onto the cornea at different angles. The fresneled axicon 1 furthermore has a central zone 1.4 that is embodied as a planar surface or as a cut-out that is provided for telecentric, distance-independent image detection.

Due to the arrangement of facets on the front and back sides, it is possible for instance to significantly increase the number of annular structures and thus also the number of measuring points. The annular structures of different radii have different facet angles in order to deflect the light towards the cornea of the eye at different angles.

Although the deflection of the light may generally be based on the principles of refraction, diffraction, and reflection, generally the principle of diffraction is not used.

The reason for this is that light diffraction on rotationally symmetrical grid structures is associated with a major drawback. The angle of deflection due to diffraction is scaled with the wavelength of the radiation used. Therefore in such a case the spectral bandwidth of the light source is limited to less than 1 nm in order to obtain precise measured values, which can be attained technically only using narrow-band light sources, such as lasers, or using additional filter elements.

Thus the following should be taken into account when estimating the necessary accuracy. The determination of the refractive effect of the cornea by measuring its curvature with a desired Accuracy <0.1 dpt corresponds to about 1/500 for a cornea having a total refractive power of 40-50 dpt. Therefore the light source, at a wavelength of e.g. 800 nm, must have a bandwidth of less than 2 nm, for example less than 1 nm. In addition, the mean wavelength must not vary more than about ±0.5 nm. To achieve these conditions for the light source, typical semiconductor laser sources that offer such a narrow band must be tempered to about 1 K, which would mean additional technical complexity.

Therefore the facet angles of the fresneled axicon are calculated such that the deflection of the light is preferably based on the principle of light refraction at small angles of deflection and at large angles of deflection is based on the principle of light reflection, at times also in combination with light refraction.

In one example embodiment, the facet angles of the fresneled axicon are calculated such that the deflection of the light at large angles of deflection is based on the principle of light reflection, so that the fresneled axicon has an additional reflecting surface.

Figure 2:
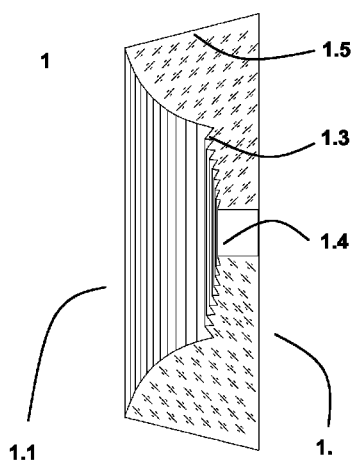
FIG. 2 is a schematic diagram of the inventive fresneled axicon having an additional reflecting surface.

To this end, FIG. 2 is a schematic diagram of the inventive fresneled axicon having an additional reflecting surface (ball).

In addition to the facets 1.3 present only on the front side 1.1, the fresneled axicon 1 has an outer facet 1.5 that acts as a common reflecting surface. The central zone 1.4 is again embodied as a planar surface or cut-out for telecentric distance-independent image detection.

Due to total reflection at the common reflecting surface for all outer zones, which is in the form of an outer facet, the light of the outer zones experiences the majority of the deflection and the final beam deflection through the facets on the front side of the fresneled axicon. Such an element makes it possible to attain more favorable conditions for the outer zones with a large angle of incidence.

A second group of example embodiments relates to the illumination unit. It for example comprises at least one light source, in particular an LED, a laser, or the outlet of an optical fiber. Since the construction is very light efficient, other types of non-point sources, such as e.g. halogen lamps and flash lamps, may be used. However, these must be limited to a spectral width of less than 50 nm by an additional filter to be able to attain precise measurement results, since the angle of refraction is also a function of the index of refraction across the dispersion of the material.

The light from the light source, which for instance has an illumination surface of about 1 mm$^2$, may be additionally stopped down by means of a circular aperture having a diameter of 100-1000 μm.

In one example embodiment, the illumination surface of the light source is variable. This may be attained for instance using a prior aperture having a variable diameter or using a plurality of light sources having different size illumination surfaces that are used alternately.

This has the advantage that the width of the rings created and reproduced on the eye may be changed. Thus for a severely deformed cornea for instance it is necessary to use very narrow rings that do not touch one another and thus permit analysis with no problem. Wider rings in this case could touch one another or even overlap, rendering analysis more difficult or even impossible.

An optical element for illuminating the entire surface of the fresneled axicon with plane waves and an optical element for separating illuminating and detecting beam paths are arranged between the illuminating unit and the fresneled axicon. The two optical elements are embodied and arranged such that illumination of the central zone of the fresneled axicon that is provided for telecentric image detection is prevented.

Figure 3:
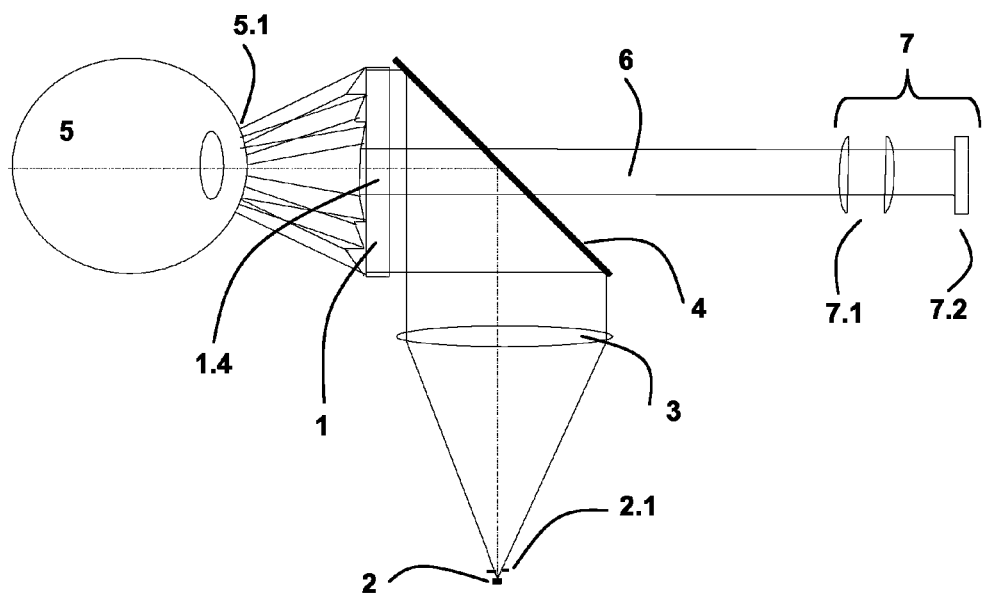
FIG. 3 is a schematic diagram of the inventive system having fresneled axicon, collimator lens, and beam splitter.

According to one example embodiment the optical element for illuminating the entire surface of the fresneled axicon with plane waves is a collimator lens. FIG. 3 is a schematic diagram of the inventive system having a collimator lens and beam splitter.

The light emitted by an LED 2 is parallelized or collimated with a collimator lens 3 and deflected towards the fresneled axicon 1 by a beam splitter in the form of a partially silvered plane-parallel plate 4. A filter 2.1 (shown in broken line) for limiting the illumination field may optionally be arranged in front of the LED 2. The partial silvering of the plane-parallel plate 4 may be embodied such that its center does not have any silvering so that illumination of the central zone 1.4 of the fresneled axicon 1 is avoided. On the other hand, if the central zone is partially silvered, in addition to the ring system a reflection point may be seen in the camera image at the apex of the cornea, which may be useful for the analysis. At the same time, however, this is associated with the drawback that the light from the detecting beam path is weakened by the partially silvered layer and thus the light efficiency is reduced. For this reason the partial silvering of the central areas of the deflection element may be adapted to the measurement properties to be achieved. The light from the LED 2 is directed at various angles onto the cornea 5.1 of the eye 5 via the annular, differently angled facets 1.3 of the fresneled axicon 1. The annular structure projected onto the cornea 5.1 of the eye 5 is reflected along the telecentric beam path 6 through the central zone 1.4 of the fresneled axicon 1, which central zone is embodied as a planar surface or cut-out, captured by the image capturing unit 7, and forwarded to the control and analysis unit (not shown) for analysis. The image capturing unit 7 has an imaging optics unit 7.1 and an image sensor 7.2 for this purpose.

Figure 4:
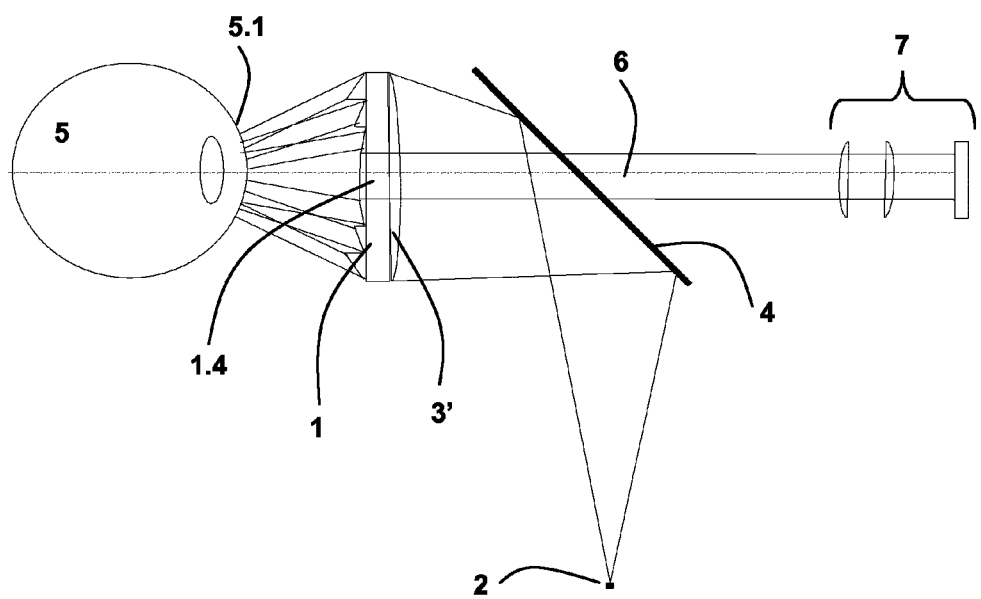
FIG. 4 is a schematic diagram of the inventive system having fresneled axicon and a beam splitter.

In one example embodiment, the collimator lens normally used as the optical element for illuminating the entire surface of the fresneled axicon may be omitted if the back side of the fresneled axicon is embodied appropriately. In this regard, FIG. 4 is a schematic diagram of a second embodiment of the inventive system having only one beam splitter.

In this case, the light emitted by an LED 2 is deflected towards the fresneled axicon 1 by a beam splitter in the form of a partially silvered plane-parallel plate 4. The back side 1.2 of the fresneled axicon 1 that is embodied as a collimator lens 3' parallelizes the light for illuminating the entire surface so that there is no need for a separate optical element. The partial silvering of the plane-parallel plate 4 may then be embodied such that its center does not have any silvering so that illumination of the central zone 1.4 of the fresneled axicon 1 is avoided. The light of the LED 2 at different angles is reproduced on the cornea 5.1 of the eye 5, and the image is captured, in the manner described in the foregoing.

Planar plates or a prism is for example used for the optical element for separating illuminating beam path and detecting beam path, wherein the planar plates or prism may have partially silvered and/or dichroitic surfaces.

With respect to the manner of functioning, it is not important whether the illuminating beam path or the detecting beam path is deflected via the optical element. However, it is more advantageous to deflect the detecting beam path, since the dimensions of the required optical elements in the form of a planar plate or a prism may be smaller. In this regard FIG. 5 is a schematic diagram of the inventive system in which the detecting beam path is deflected.

Figure 5:
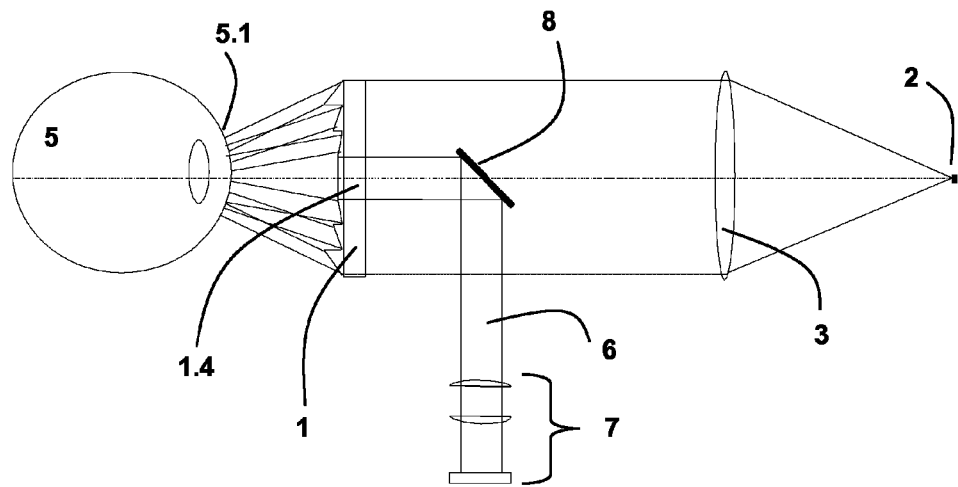
FIG. 5 is a schematic diagram of the inventive system in which the [ . . . ] is deflected with detecting beam path.

In accordance with FIG. 5, the light emitted by an LED 2 is parallelized with a collimator lens 3 and directed towards the fresneled axicon 1. The light from the LED 2 is directed at different angles onto the cornea 5.1 of the eye 5 via the facets 1.3 of the fresneled axicon 1, which facets have different angles. The annular structure projected onto the cornea 5.1 of the eye 5 is reflected along the telecentric beam path 6 through the central zone 1.4 of the fresneled axicon 1, which central zone is embodied as a planar surface or cut-out, deflected by a plane-parallel plate 8, and reproduced on the image capturing unit 7. Arranging the plane-parallel plate 8 in front of the fresneled axicon 1 prevents the central zone 1.4 of the latter from being illuminated.

Figure 6:
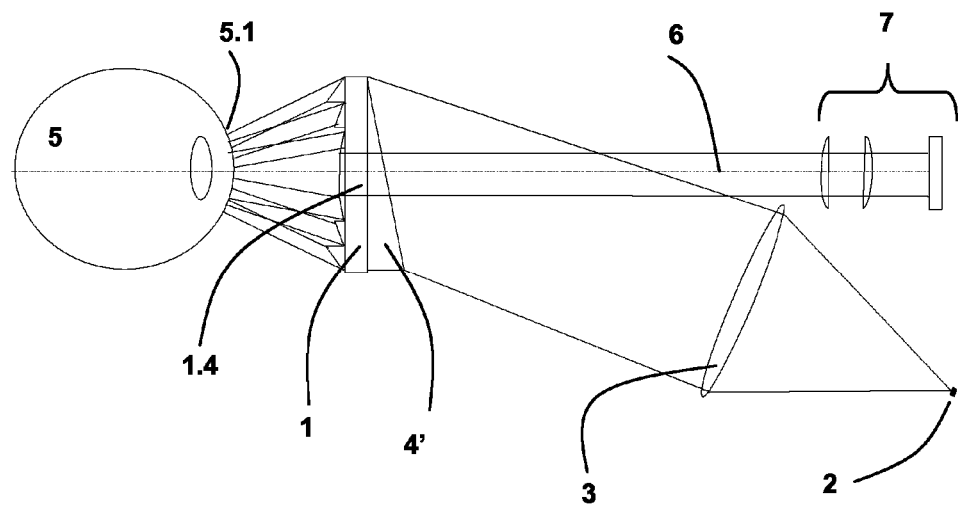
FIG. 6 is a schematic diagram of the inventive system having fresneled axicon and a collimator lens.

With this embodiment, a variant is also possible that may reduce the number of optical elements. Thus the separate optical element for separating illuminating and detecting beam paths is not needed if the back side of the fresneled axicon is embodied appropriately. In this regard, FIG. 6 is a schematic diagram of the inventive system having only collimator lens.

The light emitted by an LED 2 and parallelized by a collimator lens 3 is radiated towards the fresneled axicon 1. The collimator lens 3 may have in its center partial silvering that prevents the central zone 1.4 of the fresneled axicon 1 from being illuminated. The back side 1.2 of the fresneled axicon 1, which back side is embodied as a prism 4', separates the illuminating and detecting beam paths so that there is no need for a separate optical element for this. Both the reproduction of the light from the LED 2 at different angles on the cornea 5.1 of the eye 5 and the image capturing occur in the manner described in the foregoing in this case, as well.

Figure 7:
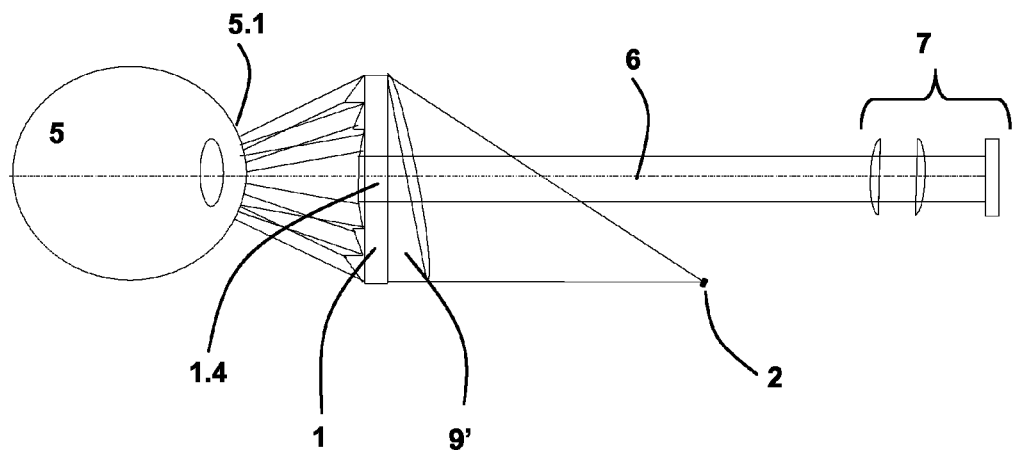
FIG. 7 is a schematic diagram of the inventive system, the fresneled axicon of which has an additional collimating and beam path separating effect.

In another example embodiment, neither a separate optical element nor separation of illuminating and detecting beam paths nor illumination of the entire surface are necessary if the back side of the fresneled axicon is embodied appropriately. In this regard, FIG. 7 is a schematic diagram of the inventive system having a fresneled axicon, the back side of which is embodied such that it has a collimating and beam-path separating effect.

The light emitted by an LED 2 is radiated towards the fresneled axicon 1. The back side 1.2 of the fresneled axicon, which back side is embodied as a wedge lens 9', separates the illuminating and detecting beam paths and also illuminates the entire surface of the fresneled axicon 1 so that it is not necessary to have a separate optical element for this purpose.

The back side 1.2 of the fresneled axicon 1, which back side is embodied as a wedge lens, has a curved annular prismatic shape that has a partial surfaces that is correspondingly silvered or dichroitic to prevent illumination of the central zone 1.4 of the fresneled axicon 1. Both the reproduction of the light of the LED 2 at different angles on the cornea 5.1 of the eye 5 and the image capturing occur in the manner known.

In another example embodiment, the facets are embodied on the front side of the fresneled axicon such that the latter has an aspheric effect for correcting imaging errors. Using this it is possible to correct imaging errors such as color errors, recording errors, and the like.

A third group of example embodiments relates to the image capturing unit, which as a rule comprises an imaging optics unit and an image sensor. The central zone of the fresneled axicon is embodied as a hole or planar surface for telecentric image capturing.

Figure 8:
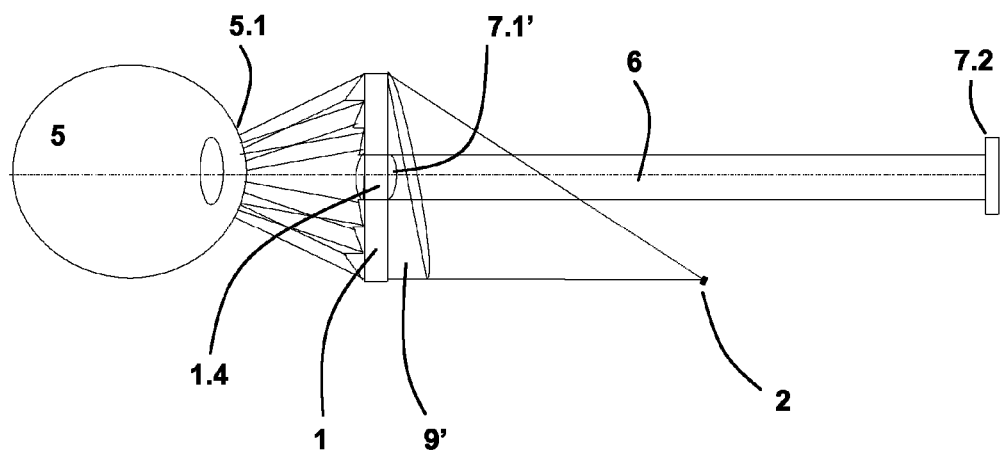
FIG. 8 is a schematic diagram of the inventive system, the imaging optics for image detection being integrated in its fresneled axicon.

However, it may also be advantageous when the central zone of the fresneled axicon has an optical function. The central zone may be embodied for instance as a filter or even as an imaging optics unit. In this regard, FIG. 8 is a schematic diagram of the inventive system that has the imaging optics unit for image capturing integrated in its fresneled axicon.

In accordance with the solution described in FIG. 7, the light emitted by an LED 2 is radiated directly onto the back side 1.2 of the fresneled axicon 1, which back side is embodied as a wedge lens 9'. The light from the LED 2 is reproduced at different angles on the cornea 5.1 of the eye 5 and reflected thereby along the telecentric beam path 6 onto the image sensor 7.2 of the image capturing unit 7. Since the central zone 1.4 of the fresneled axicon 1 is embodied as an imaging optics unit 7.1, there is no need for a separate imaging optics unit.

As described in the foregoing, the image of the annular structure reflected by the cornea 5.1 of the eye 5 that is captured by the image sensor 7.2 is forwarded to the control and analyzing unit (not shown) for analysis.

Figure 9:
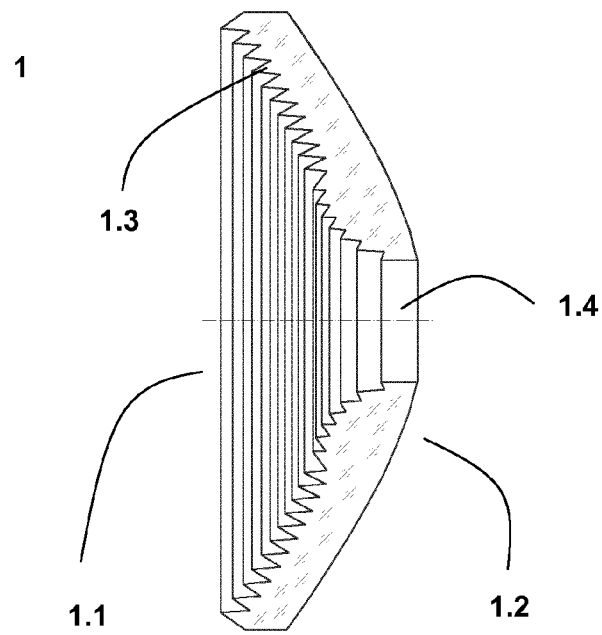
FIG. 9 is one example embodiment of the inventive fresneled axicon, the front side of which has facets and back side of which has an aspherical shape.

FIG. 9 illustrates one another example embodiment. The fresneled axicon 1 depicted here is embodied such that its front side 1.1 has facets 1.3 and its back side 1.2 has an aspherical shape and the fresneled axicon 1 also has a curved or tapered shape overall. In this case, the wave radiated by the light source is collimated by an asphere on the back side 1.2 and the annular plane waves are deflected by the facets 1.3 of the fresneled axicon 1 that are embodied on its front side 1.1. However, the light of the outer 11 zones is attained not via refraction on the fresneled axicon 1, but rather by a combination of total reflection and refraction on 2 facets 1.3 of the fresneled axicon 1.

Figure 10:
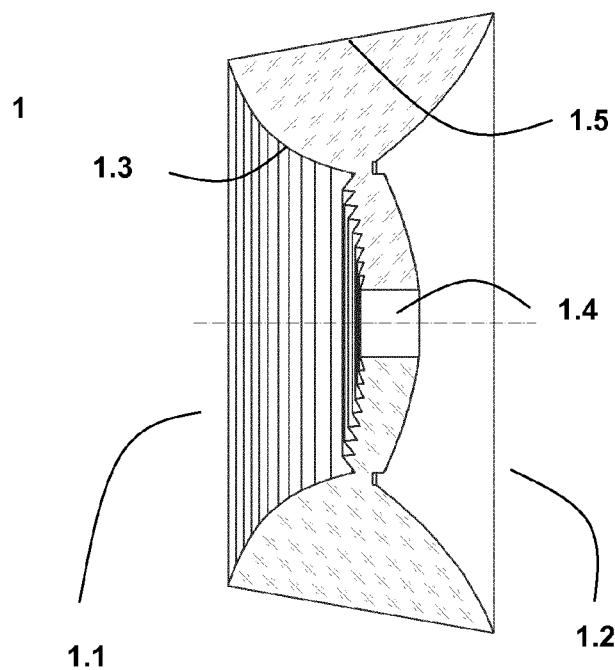
FIG. 10 is another example embodiment of the inventive fresneled axicon, which has a common outer facet for all zones in addition to facets on the front side and an aspherical shape on the back side.

FIG. 10 illustrates another example embodiment. The fresneled axicon 1 illustrated here represents modification of the structure in FIG. 9 and is characterized in that the light of the outer 11 zones experiences the majority of the deflection by total reflection on the outer facets 1.5 that are common for all outer zones and the final beam deflection is attained using each facet 1.3 on the front side of the fresneled axicon 1. This form for the fresneled axicon 1 has the advantage that it makes possible more favorable conditions for the outer zones with a wide angle of incidence onto the cornea.

Figure 11:
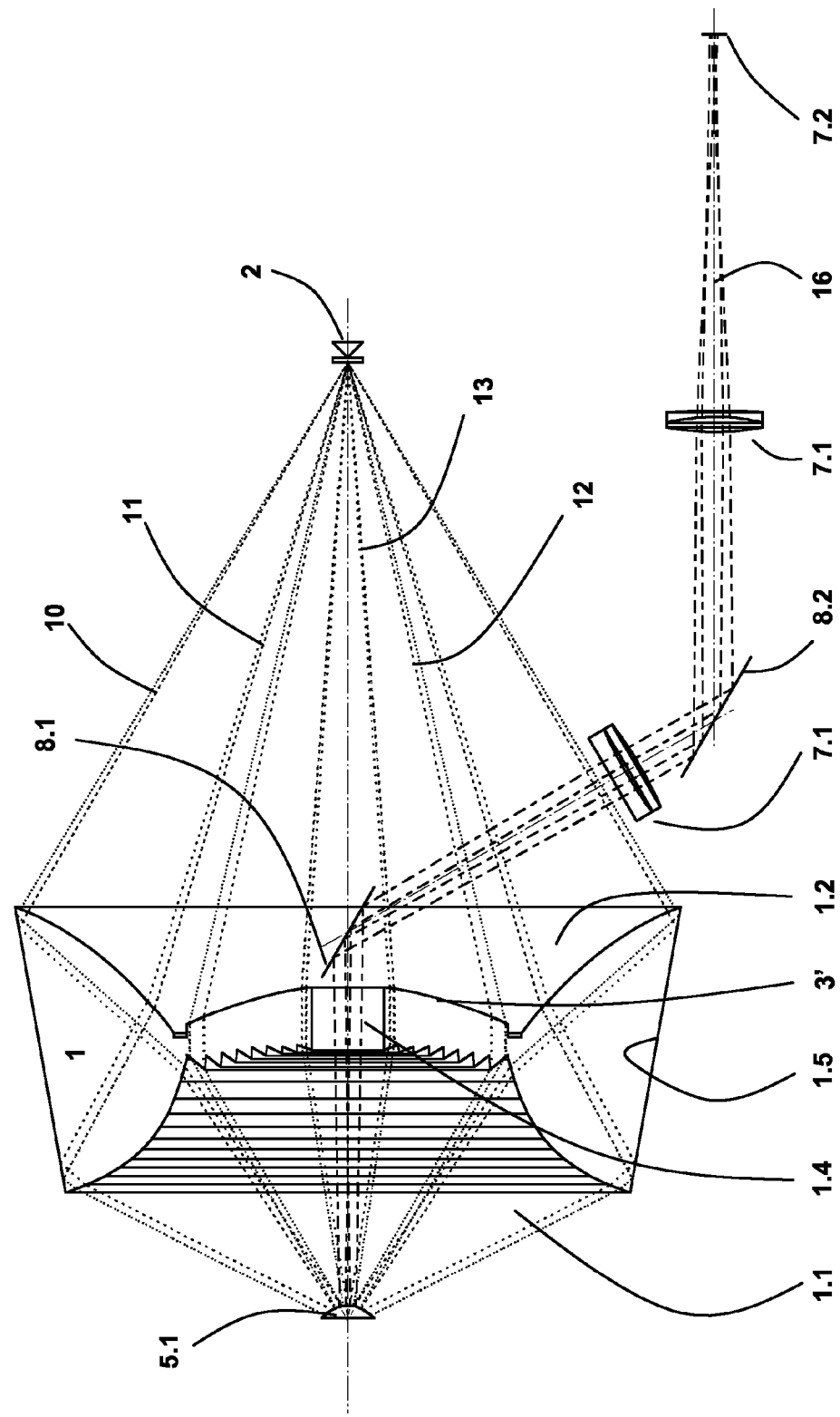
FIG. 11: is an example beam guidance for illumination and detection for the embodiment in accordance with FIG. 10.

FIG. 11 depicts another example beam guidance for illumination and detection for the embodiment in accordance with FIG. 10. The light emitted by an LED 2 is radiated towards the fresneled axicon 1. The back side 1.2 embodied as a collimator lens 3' parallelizes the light for illuminating the entire fresneled axicon 1 so that there is no need for a separate optical element for this purpose. Due to total reflection on the outer facet 1.5 that is common for all zones, the light bundles 10 and 11 of the outer zones experience the majority and each through a facet 1.3 on the front side of the fresneled axicon 1 experience the final deflection for forming an image on the cornea 5.1. In contrast, the light bundles 12 and 13 from the inner zones are merely deflected by one facet 1.3 each. The annular structure projected onto the cornea 5.1 of the eye 5 is reflected as a beam bundle 16 through the central zone 1.4 of the fresneled axicon 1, which central zone is embodied as a planar surface or cut-out, and deflected by a first plane-parallel plate 8.1 via an imaging optics unit 7.1 towards the image sensor 7.2. A second plane-parallel plate 8.2 is disposed in the imaging optics unit 7.1. A very compact arrangement is achieved by deflecting the detection beam path twice.

In another variation, the fresneled axicon may be embodied such that both the collimating effect for the light source and the deflecting effect for the beam deflection towards the cornea occur on only one side, for instance the front side, of the fresneled axicon.

With the inventive solution a system for determining the surface shape of the cornea of an eye is made available, which system is based on a Placido disk and an image capturing unit with telecentric image detection, which has higher light efficiency with a simpler and more cost-effective structure, and that nevertheless permits essentially distance-independent measurements of corneal topography.

Using a Placido disk-like element generates a large number of measurement points, which necessarily leads to an increase in the accuracy of the determination of the topography of the cornea.

The suggested system for determining the surface shape of the cornea of an eye thus combines the advantage of a topographs based on a Placido disk (large number of measurement points) with the advantage of a Littmann keratometer (distance-independent measurements). This may be achieved in that the Placido disk is embodied as a fresneled axicon having annular structures of different radii that image the light of a single light source at different angles towards the cornea of the eye.

The special advantage of the inventive system for determining the topography of the cornea of an eye is particularly that the suggested formation of the annular structure occurs without any absorption, i.e. only by light forming and guidance, only a single light source being needed.

Although the suggested system is provided in particular for determining the topography of the cornea of an eye, it may be used for determining the topography of any reflecting bodies.

A topograph based on a Placido-disk supplies a signal with the typical rings for all distances from the device to the eye. However, measuring errors that are scaled with the distance to the optimum focus/adjustment point occur due to the dependence on distance.

In the distance-independent system illustrated here, similar to keratometers according to Littmann, it is possible to see the effect that there are shadowing effects for greater distance deviations to the optimum adjustment point and no rings are visible in the camera image. As soon as the adjustment point is moved back closer, the rings are visible and very precise measured values may be calculated therefrom, independent of distance.

The area in which no shadowing effects occur largely depends on the width of the annular "planar" beam bundle and the mean angle for the zone in question. It is therefore preferred to optimize the width of the zones independently of one another to a free setting range that is as large as possible to enable robust measurements of restless eyes. Therefore the outer zones, e.g. in accordance with FIGS. 9 and 10, are clearly embodied wider than the inner zones. For certain measuring devices it may be necessary to enable a much more robust setting for a reduced number of rings to be measured. For this reason it may be advantageous to have an element with only a few widths, but widths that are clearly wider. Elements with only 3 rings/zones are possible, for instance.

In addition, each of the depicted structures may be scaled such that a certain adjustment insensitivity may be achieved for a certain number of zones.

Moreover, it is also possible to adjust the adjusting range of the different zones to different values and to use the number of non-shadowed zones in the camera image to attain automatic or semiautomatic positioning of the device in front of the eye. Thus for instance the maximum and minimum number of zones seen in the camera image may be used as a control signals for an axial actuating drive.

However, due to the rotationally-symmetrical grid structures of the fresneled axicon, the adjusting range is also reduced in size so that restless patients and patients whose eyes have very highly aspheric deviations, of for instance 15 dpt, cannot be measured.

Due to the rotationally-symmetrical grid-structures, spherical waves are radiated onto the eye that are collimated and flat in each section through the optical axis. It is precisely using these waves that are planar in the section that the distance-independence of the method is achieved since all beams in the bundle have the same angle of incidence onto the cornea. Due to the rotationally-symmetrical spherical shape of the wave, however, given lateral decentration of the eye the light is reflected on the cornea in directions that no longer travel into the detecting optics unit. This causes shadows in the detector image that lead either to it not being possible to obtain any measurements at all or to the measurements being distance-dependent and therefore imprecise. Similar shadows occur with highly aspheric corneal shapes that act like a local decentration.

In the invention, this problem is solved in that the wave is shaped in the fresneled element such that in every section through the optical axis the wave remains a plane wave, but in the azimuthal direction it is no longer completely focused in a sphere. This can only be achieved by giving up rotational symmetry of the Fresnel disk.

This is for example accomplished in that one of the two optically active surfaces of the fresneled axicon also has a non-rotationally symmetrical structure. This applies for all of the variants of the fresneled axicon that were described in the foregoing.

In a first embodiment, one of the two optically active surfaces of the fresneled axicon also has a diffractive structure in the form of a diffraction grid, the grid lines of which run radially and the grid vectors of which run azimuthally on each location. In one further example embodiment, diffraction grids are used that have different local frequencies.

In a second example embodiment, one of the two optically active surfaces of the fresneled axicon also has a sinusoidal structure that runs radially. The modulation depth of the sinusoidal structure is between a few µm and a few 100 µm and its wavelength is between 0.1 mm and 20 mm. For example, the wavelength is approximately 2 mm.

The essential feature of this second example embodiment is that due to the azimuthal structures, in each section the partial waves remain completely collimated by the optical axis, while in the plane perpendicular thereto they are not focused in a sphere onto the optical axis. The wave may be focused e.g. on real and virtual points clearly in front of or behind the optical axis (and therefore may also be defocused) or may also be completely collimated.

In a third example embodiment, one of the two optically active surfaces of the fresneled axicon also has a structure in the form of many plane facets that are adjacent to one another. In this case as well, the modulation depth of the sinusoidal structure is between a few µm and a few 100 µm and its wavelength is between 0.1 mm and 20 mm. According to another example embodiment the wavelength is approximately 2 mm.

In this embodiment, per facet many partial waves collimated in both spatial directions are generated by the fresneled axicon, instead of one "wedge-shaped" plane wave. If the cornea of the eye is illuminated with these waves and detection is performed with a telecentric detection optics unit, annular point chains result in the detector image. The essential feature of this embodiment is that a great number of partial waves that are completely collimated in both directions are generated by the structure.

Another essential advantage of the facetted structures is that highly aspheric surfaces may be measured, which provides the opportunity for instance to measure very severe cylinder errors on the order of 15 dpt. In addition, this more robust measurement also enables the evaluation of more severe local shape abnormalities as occur e.g. with inhomogeneities or when the tear film is broken up.

A third significant advantage of the facet structure is enabled by the point-chain-shaped detection pattern. This pattern modulates the detection rings that are known from Placido disks according to the prior art and in addition to being able to determine the diameter of the circle in the detector image, it is also possible to determine the angular coordinates of each spot. With these data it is even possible to correct "skew" rays and thus the errors in topographs that are based on Placido disks and are known as "skew ray errors."

Because of this, it is possible to connect the topographical measured values to a topography not only along the meridians, but also azimuthally along the point chains. This can significantly increase the accuracy of the topography, especially for highly aspherically shaped test specimens. Thus, if the desire is just to configure the element so that it is possible to achieve very robust measurements on highly aspherical corneas, embodiment 1 or 2, which embodiments are technically easier to realize, is used. If there is a desire to correct the "skew ray error," the technically more challenging embodiment 3 is used.

If e.g. a structure in accordance with FIG. 9 is realized, the light is deflected in the outer zones of the element via a combination of total reflection and refraction. In this case, in order to generate many partial waves that are plane in both transverse directions, both surfaces would have to be so structured. Producing such a component is technically very complex, however. Since the majority of the light deflection is produced by total reflection, in this case it is possible to design the refracting surface rotationally symmetrical and to optimize the total reflecting surface with facets such that many partial waves that are plane in both directions are emitted from the disk. In this case the total reflecting surface does not constitute adjacent plane facets but rather adjacent free-form surfaces.

The suggested system for determining the surface shape of the cornea of an eye thus not only combines the advantage of a topograph based on a Placido disk (plurality of measurement points) with the advantage of a Littmann keratometer (distance-dependent measurement), but also provides the opportunity for essentially distance-independent measurements in a larger measuring area, even for severe asphericity.

All three of the embodiments described offer the advantage that shadow artifacts do not occur until about 10× stronger decentrations than without additional structures.

The invention claimed is:

1. A system for determining the topography of the cornea of an eye, comprising:
   an element having a fresnel structure for generating rings similar to a Placido disk that are reflected from the cornea;
   an illuminating unit arranged in an illuminating beam path;
   an image capturing unit arranged in a detecting beam path;
   a control and analysis unit;
   wherein the element for generating rings similar to a Placido disk comprises a fresneled axicon including annular structures of different radii that image light of the illuminating unit at different angles at the cornea of the eye, the fresneled axicon having at least one conical refractive surface; and
   further comprising a first optical element that illuminates an entire surface of the fresneled axicon with annular plane waves;
   a second optical element that separates illuminating and detecting beam paths, the first optical element and the second optical element being arranged between the illuminating unit and at least one surface of the fresneled axicon; and
   the image capturing unit, comprising an imaging system and an image sensor being structured for telecentric, distance-independent image detection.

2. The system in accordance with claim 1, wherein the annular structures of different radii in the form of facets having different facet angles are arranged on front sides of the fresneled axicon, back sides of the fresneled axicon or both front sides and back sides of the fresneled axicon.

3. The system in accordance with claim 1, wherein the facet angles of the facets of the fresneled axicon are calculated such that deflection of annular plane light waves is based on a principle of at least one of refraction, diffraction, or reflection.

4. The system in accordance with claim 1, wherein the facet angles of the facets of the fresneled axicon are calculated such that deflection of the light is based on a principle of light refraction at small angles of deflection and at large angles of deflection is based on a combination of light reflection and light refraction.

5. The system in accordance with claim 1, wherein the facet angles of the facets of the fresneled axicon are calculated such that the deflection of the light at large angles of deflection is based on the principle of light reflection on a surface that is common for all zones, for which purpose the fresneled axicon comprises an additional reflecting surface.

6. The system in accordance with claim 1, wherein the illumination unit further comprises a light source that is in front of a variable diameter aperture.

7. The system in accordance with claim 1, wherein the illumination unit comprises a plurality of light sources having different size illumination surfaces that are alternately usable.

8. The system in accordance with claim 1, further comprising an optical element that illuminates an entire surface of the fresneled axicon with annular plane waves comprises a collimator lens.

9. The system in accordance with claim 1, wherein a back side of the fresneled axicon is structured to incorporate the first optical element and a front side of the fresneled axicon comprises the entire surface of the fresneled axicon that is illuminated with annular plane waves.

10. The system in accordance with at claim 8, wherein a ratio of an illumination surface of the light source to a focal distance of the collimator lens is between 1:20 and 1:100.

11. The system in accordance with at claim 10, wherein a ratio of an illumination surface of the light source to a focal distance of the collimator lens is between 1:100 and 1:250.

12. The system in accordance with claim 1, wherein the second optical element for separating the illuminating beam path and the detecting beam path comprises a planar plate or a prism having partly silvered surfaces, dichroitic surfaces or a combination of partly silver surfaces and dichroitic surfaces.

13. The system in accordance with claim 1, wherein a back side of the fresneled axicon is structured such that the optical element for separating illuminating beam path and detecting beam path is incorporated therein.

14. The system in accordance with claim 1, wherein a back side of the fresneled axicon is structured such that both the optical element for separating illuminating beam path and detecting beam path and the collimator lens are incorporated therein.

15. The system in accordance with claim 1, wherein facets on a front side of the fresneled axicon are structured such that the facets have an aspherical effect for correcting imaging errors, for collimating the illumination light or both of the foregoing.

16. The system in accordance with claim 1, wherein a central zone of the fresneled axicon structured for telecentric image detection comprises a hole or plane surface.

17. The system in accordance with claim 1, wherein a central zone of the fresneled axicon structured for telecentric image detection is structured such that the imaging system of the image capturing unit is incorporated therein.

18. The system in accordance with claim 1, wherein a width of a bundle striking the cornea is adjusted such that a free adjusting area of the eye is maximized.

19. The system in accordance with claim 1, wherein the free adjusting area is designed differently for zones such that shadowing effects of the zones are detected, analyzed, and used as a control signal for automatic or semiautomatic positioning of the system in front of the eye.

20. The system in accordance with claim 1, wherein optically effective surfaces of the fresneled axicon have a minimized scattering effect.

21. The system in accordance with claim 1, wherein the fresneled axicon is rotationally asymmetrical.

22. The system in accordance with claim 21, wherein one of two optically active surfaces of the fresneled axicon also has a rotationally asymmetrical structure.

23. The system in accordance with claim 1, wherein one of two optically active surfaces of the fresneled axicon further comprises a diffractive structure in the form of a diffraction grid, grid lines of which run radially and grid vectors of which run azimuthally at each location.

24. The system in accordance with claim 23, wherein the diffraction grid has locally different frequencies.

25. The system in accordance with claim 1, wherein one of two optically active surfaces of the fresneled axicon further comprises a sinusoidal structure that runs radially.

26. The system in accordance with claim 25, wherein a wavelength of the sinusoidal structure is between 0.1 mm and 20 mm.

27. The system in accordance with claim 26, wherein the wavelength of the sinusoidal structure is approximately 2 mm.

28. The system in accordance with claim 1, wherein one of two optically active surfaces of the fresneled axicon further comprises a structure in the form of many adjacent plane facets.

29. The system in accordance with claim 28, wherein a wavelength of the facet structure is between 0.1 mm and 20 mm.

30. The system in accordance with claim 29, wherein the wavelength of the facet structure is approximately 2 mm.

31. The system in accordance with claim 1, wherein one of two optically active surfaces of the fresneled axicon further comprises a structure in the form of many adjacent free-form surfaces.

\* \* \* \* \*

UNITED STATES PATENT AND TRADEMARK OFFICE
CERTIFICATE OF CORRECTION

PATENT NO. : 9,084,564 B2  
APPLICATION NO. : 14/119367  
DATED : July 21, 2015  
INVENTOR(S) : Daniel Bublitz et al.

It is certified that error appears in the above-identified patent and that said Letters Patent is hereby corrected as shown below:

In the Specification

Col. 3, line 46, after "there", insert --are--

Col. 9, delete "one"

Signed and Sealed this  
Twelfth Day of April, 2016

Michelle K. Lee  
*Director of the United States Patent and Trademark Office*